United States Patent [19]

Yamauchi et al.

[11] 4,292,973

[45] Oct. 6, 1981

[54] APPARATUS FOR REFRIGERATION TREATMENT

[75] Inventors: Toshima Yamauchi, Oita; Sadao Nogami, Beppu; Kengi Sawada, Oita; Jyunichiro Moriya, Kokubunji; Hiroomi Sawada, Ichikawa; Keizou Kobayashi, Hanno, all of Japan

[73] Assignee: Kabushiki Kaisha Kurio-Medikaru, Tokyo, Japan

[21] Appl. No.: 109,271

[22] Filed: Jan. 3, 1980

Related U.S. Application Data

[63] Continuation of Ser. No. 944,079, Sep. 20, 1978, abandoned.

[30] Foreign Application Priority Data

Sep. 25, 1977 [JP] Japan .............................. 52-114967
Feb. 28, 1978 [JP] Japan .............................. 53-22900

[51] Int. Cl.³ .......................................... A61B 17/36
[52] U.S. Cl. ................................................ 128/303.1
[58] Field of Search ............... 128/303.1, 399; 165/34, 165/35, 173

[56] References Cited

U.S. PATENT DOCUMENTS

| 2,319,542 | 5/1943 | Hall | 128/303.1 |
| 3,398,738 | 8/1968 | Lamb et al. | 128/303.1 |
| 3,812,854 | 5/1974 | Michaels et al. | 128/194 |
| 4,063,560 | 12/1977 | Thomas et al. | 128/303.1 |

FOREIGN PATENT DOCUMENTS

| 1443070 | 7/1976 | United Kingdom | 128/303.1 |
| 364317 | 2/1973 | U.S.S.R. | 128/303.1 |
| 424563 | 10/1974 | U.S.S.R. | 128/303.1 |

Primary Examiner—Robert W. Michell
Assistant Examiner—Thomas Wallen
Attorney, Agent, or Firm—Haseltine and Lake

[57] ABSTRACT

An apparatus for refrigeration treatment is used in cryomedical treatment for applying gas of extremely low temperature onto an affected portion of the flow patient. In a system of the apparatus, there are a liquefied gas source, a temperature controlled bath and a conduit pipe having a cup at its end to be placed over the affected portion. The bath contains a liquid medium of high specific heat in which are immersed a mixing cylinder and an evaporator which are mutually connected with a plurality of tubes. The liquefied gas supplied from the source to the evaporator is vaporized and flowed through the tubes to the cylinder where the vaporized gas is mixed with a liquefied gas directly supplied from the source at an optimum gas temperature.

2 Claims, 6 Drawing Figures

APPARATUS FOR REFRIGERATION TREATMENT

This is a continuation of application Ser. No. 944,079 filed Sept. 20, 1978, now abandoned.

BACKGROUND OF THE INVENTION

This invention relates to an apparatus for refrigeration treatment, particularly to an apparatus by which cryogenic air is provided and applied to an affected portion at high speed.

In medical treatment of sprains, rheumatism, contusions, neuralgia and other diseases, successful results are obtained by cooling an affected portion with a cryogenic gas applied at high speed and in a short time. In this type of treatment it is sometimes required to apply a cryogenic temperature of $-80°$ C. to $-190°$ C. to an affected portion.

Generally, a simple method of obtaining a cryogenic temperature for medical treatment is to use ice or a refrigerant, but it does not offer the cryogenic temperature and consequently, cryogenic air obtained from a refrigerator or cryogenic carbon dioxide gas obtained by blowing out liquefied carbon dioxide gas is used. However, it is not easy to obtain such cryogenic temperature as can meet the above requirement. If the application is simply to cool the affected portion, it is possible to apply liquefied gas to the affected portion by utilizing the cryogenic latent heat produced in vaporization of liquefied gases such as liquid oxygen (boiling point $-183°$ C.) or liquid nitrogen (boiling point $-196°$ C.).

If these gases are used for medical treatment in a small treatment room however, the room will be filled with gas. The former gas may involve the danger of fire and the latter gas may cause lack of oxygen in the room. Thus, it is not desirable to use these gases for medical treatment in the manner mentioned above.

SUMMARY OF THE INVENTION

The present inventors decided to utilize commercially available liquefied air, which would cause no harm to individuals even when it is used in a room and fills the room and yet produces appropriate effects of refrigeration treatment of an affected portion and which is available at a relatively low cost. To refrigerate an affected portion for medical treatment, it is necessary to change the cooling temperature to be applied to the affected portion in accordance with the degree of the disease or ailment. Furthermore, for efficient treatment of same, it is also necessary to be able to change the refrigerating gas temperature in a short time in the preparation of the medical treatment. This requires obtaining air of the aforementioned optimum temperature of $-80°$ C. to $-190°$ C. suitable for medical treatment in a short time by producing cryogenic air from liquefied air, whose boiling point temperature is approximately $-193°$ C. Liquefied air is obtainable from liquefied oxygen and liquefied nitrogen by mixing these liquefied gases at approximately the same mixing ratio as that of oxygen to nitrogen in the air. But generally speaking, it is difficult to rapidly change the temperature of low temperature air in such wide range of temperature.

In our daily life, when water poured into a cup is too hot for drinking or gargling, we cool it by adding cold water into the cup to make the temperature suitable for drinking or gargling, instead of waiting for the hot water to cool naturally. Based on this principle, the present inventors carried out experiments, assuming that air below the aforementioned temperature of $-80°$ C. suitable for medical treatment would be obtained by mixing ordinary atmospheric air with cryogenic air which has just vaporized.

Air of the intended optimum cryogenic temperature can be obtained in this manner. In order to apply the cryogenic air thus-obtained to an affected portion, it is necessary to introduce the cryogenic air into a conduit or hose and apply this cryogenic air to the affected portion through a cup provided on the end of the conduit. Since air in the atmosphere contains moisture, however, moisture in the atmospheric air will be mixed with the cryogenic air and clog the conduit with the moisture frozen in the conduit, thus making it impossible to blow out the gas from the cup. Furthermore, when the mixed cryogenic air is blown onto the affected portion, moisture in the mixed gas will freeze the affected portion upon contact therewith. This makes it necessary to remove the moisture in the warmer air. Removal of moisture in the atmosphere can be accomplished by use of a dehumidifier. To remove moisture completely by this dehumidifier, it must be installed in the treatment room or in an adjacent room in use. It is, however, troublesome for a doctor engaged in medical treatment or an assistant doctor or nurse to supervise the operation of this apparatus. Since moisture has been removed from liquefied air, sold on the market, during its liquefying process, there is no moisture to freeze when gas obtained by vaporizing liquefied air is introduced into a conduit. The present invention was made by taking advantage of this point. If the conduit for feeding the cryogenic gas takes a long time to apply such a cryogenic gas to an affected portion, the conduit is heated by the temperature of the room in which treatment is made, with the result that the temperature of the gas discharged or blown out from the end of the conduit increases. It is therefore necessary to make the length of the conduit to feed the gas as short as possible. However, even the slightest carelessness may allow liquefied gas not yet vaporized to reach the affected portion. This also involves danger.

The present invention was made with this problem taken into account and is provided with an evaporating apparatus for evaporating liquefied gas introduced from a reservoir into the flow path for feeding cryogenic gas the evaporating apparatus being so constructed that a valve mechanism is provided to prevent inflow of the liquid into the evaporating apparatus when the liquid of the liquefied gas fed to the apparatus reaches a specified volume. In the valve mechanism there is used an electromagnetic valve, check valve or the like designed to prevent inflow of excessive liquid into the evaporating apparatus so that a large amount of fluid fed to the evaporating apparatus from upstream, i.e., from the reservoir in the form of liquid, does not flow downstream from the apparatus in the form of liquid without being vaporized completely in the evaporating apparatus.

On the downstream end of the flow path to feed the cryogenic gas of the refrigeration treatment apparatus according to the present invention, a cup is provided for application to the affected portion of a patient in a prone position or kneeling down on one knee. Here, the flow path connecting to the cup may preferably be a flexibe tube. A rubber or plastic material which is a flexible and thermally insulating material at ambient temperature cannot maintain flexibility at the cryogenic temperature mentioned above. Furthermore, a conduit to be used at such a cryogenic temperature must be large in outside diameter though small in inside diameter, because the insulating layer surrounding the conduit is thick. It is hardly possible to expect such a conduit to be flexible. Instead, it is rigid. Thus, the flow path in the present invention is provided, on the flow path end to which the cup is directly fitted and in the upstream rigid flow path portion, with at least one set of joint assemblage comprising the first joint which turns around the flow path axis and air-tightly communicates with the flow path and the second joint which turns in the plane intersecting the axis of the joint at right angles and which air-tightly communicates with the first joint to form a flow path toward downstream.

DESCRIPTION OF THE PREFERRED EMBODIMENTS

Figure 1:
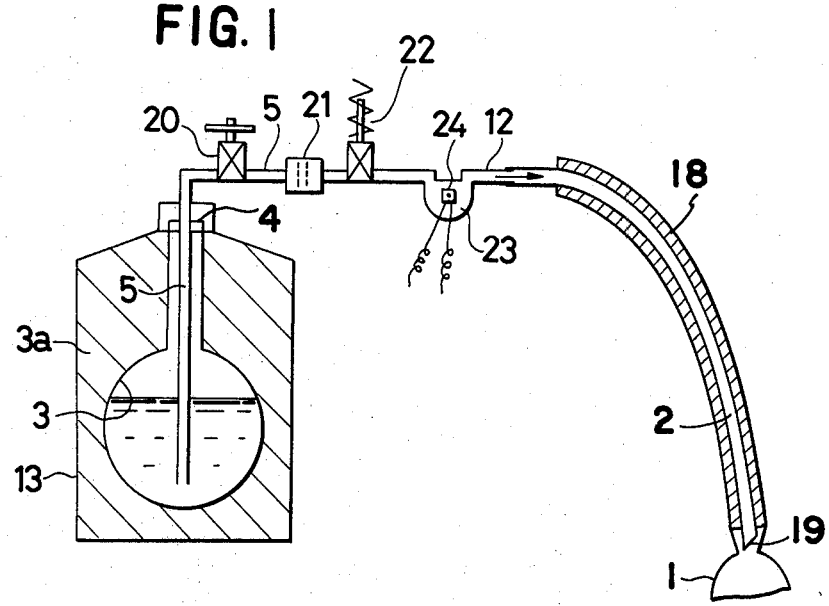
FIG. 1 is a schematic diagram showing the general arrangement of the apparatus according to present invention.

The liquefied gas source of air, oxygen or nitrogen is housed in a vessel (3), the vessel (3) being surrounded by a protective cylinder (13) and heat insulating material (3a) is filled between the vessel (3) and the protective cylinder (13) for heat retention. An exhaust tube (5) is provided at the discharge port (4) of the vessel (3) via valve (20). Filter (21) is installed in the conduit (5) to remove small pieces of ice, dust particles and other foreign objects contained in the liquefied gas. The discharge port (12) connects to a conduit (2) connected to a cup (1) to be applied to an affected portion. The conduit (2) is a tube or conduit covered with a heat insulating material (18) for heat retention. The end of the conduit (2) is connected to the cup (1) via a non-return-type expansion valve (19). One important point of this embodiment is the provision of an evaporating apparatus comprising an electromagnetic valve (22) installed in the conduit (5) downstream of the filter (21) and an evaporating chamber (23) installed in the conduit (5) downstream of the valve (22). In the evaporating chamber (23) is provided a detecting float (24a) which floats in the liquefied gas fed from the reservoir (13) through the conduit (5). This float is so designed that it rises in the evaporating chamber (23) with rise of the liquefied level when the liquid gas fed into the evaporating chamber (23) accumulates to a specified volume to raise the level and generates an electric signal when it comes in contact with, for example, the ceiling of the evaporating chamber (23) or the like. When the liquefied gas fed to the evaporating chamber (23) accumulates in the chamber (23) and is heated by the temperature of the external air and other air through the evaporating chamber wall, the liquefied gas vaporizes and the vaporized gas flows downstream from the outlet (12) of the evaporating chamber (23) through the conduit (2).

Figure 2:
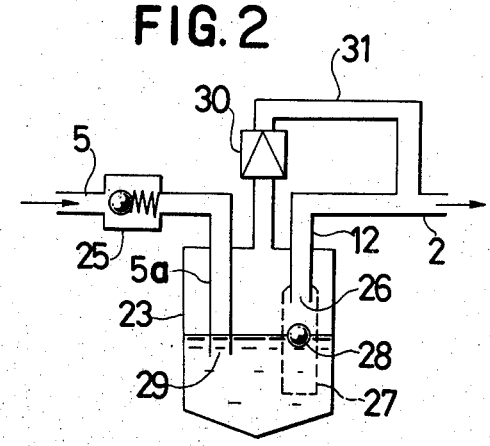
FIG. 2 is a schematic diagram showing another evaporating mechanism of the liquid gas.

Describing the actions of the evaporating apparatus mentioned above, the liquefied gas discharged from the reservoir (13) in the form of liquid passes through the conduit (5) and enters the evaporating chamber (23) through the electromagnetic valve (22) which is normally open. The liquefied gas is vaporized in the evaporating chamber (23), heated by the outside air as mentioned above, and flows downstream from the outlet of the evaporating chamber (23), for example, toward the conduit end where the cup (1) is provided. As long as the liquefied gas is demanded continuously at the conduit end, the liquefied gas flows smoothly into the evaporating chamber (23) and is evaporated in the chamber (23) to be discharged downstream. However, the liquid may flow excessively into the evaporating chamber (23) for some reason. In this case, the liquid fed to the evaporating chamber (23) constantly accumulates in the chamber (23). As the liquid accumulates in the evaporating chamber (23), the float (24) rises with rise of the liquid level until it comes in contact with, for example, the ceiling of the evaporating chamber or another area. of the chamber (23) and generates an electric signal, thereby the electromagnetic valve (22) is closed to prevent the liquefied gas from the reservoir (13) from flowing into the evaporating chamber (23). If the electromagnetic valve (22) is not closed in this case, the liquefied gas will gush out from the cup in the form of liquid, causing serious trouble. If the vaporized gas does not flow smoothly downstream, the internal pressure of the evaporating chamber (23) will increase by the pressure of the vaporized gas. Although this increased pressure so functions as to push back the liquefied gas fed to the evaporating chamber (23) to the reservoir (13), with further increase in pressure the pressurized gas will flow into the reservoir (13), causing an abrupt increase of the reservoir pressure and large quantities of liquefied gas in the reservoir (13) to gush out. However, this evaporating apparatus detects only the rise of the liquid level of the evaporating chamber (23) and closes the electromagnetic valve (22) by the signal the float sends out when a specified liquid level is reached, so that the liquefied gas does not flow back upstream and the liquefied gas in the reservoir (13) is prevented from gushing out. Since the circuitry and mechanism for operating the electromagnetic valve (22) by a signal produced by the float (24) can be created by those skilled in the art without inventive conception, details of same have been omitted. In an embodiment other than the above embodiment, where the liquefied gas in the evaporating chamber (23) has a temperature difference between a gaseous state and a liquid state, a resistor element, whose electric resistance changes with changes of temperature due to the endothermic difference caused by the difference of substances, is arranged in such a manner that it is in contact with the gas at all times and comes in contact with the liquid if the liquid level in the evaporating chamber rises. In this manner, when the resistor element in the gaseous atmosphere comes in contact with the liquid, a signal is generated by the change in resistance and the electromagnetic valve (22) can be closed by this signal. This structure does not make it necessary to place the evaporating chamber (23) in a horizontal position for correct operation of the float floating in the liquid. FIG. 2 is a schematic illustration of another evaporating apparatus, in which evaporating chamber (23) is provided in conduit (5). Upstream of this evaporating chamber is provided a check valve (25) and the liquid fed through the conduit (5) flows into the evaporating chamber (23) from an inflow path (5a) through valve (25). The gas vaporized in the evaporating chamber (23) is fed to the extension portion (2) of the conduit (5) from the outlet (26) through the outflow path (12). In the area under the outflow port (26) there is an enclosure (27) such as a grid or the like, in which float (28) is placed. The inflow port (29) of the inflow path (5a) is opened below the outlet (26). The float (28) floats in the liquid fed to the evaporating chamber (23) and rises with the rise of the liquid level so as to block the outlet (26). Numeral (30) is a pressure valve closed at all times, which is installed in a bypass (31) connecting the evaporating chamber (23) with the downstream conduit (2). Describing the actions of this embodiment, the liquid gas discharged from the reservoir (13) is fed from the conduit (5) to the evaporating chamber (23) through the check valve (25). Since the inflow port (29) of the inflow path (5a) is opened in the lower portion, the port (29) is immersed in the liquid when the liquid accumulates in the evaporating chamber (23) so that the gas vaporized in the evaporating chamber (23) does not fill the inflow path (5a). The gas vaporized in the evaporating chamber (23) flows downstream from the outlet (26) through the outflow path (12). Here, if the inflow of the liquid becomes excessive for some reason, the liquid fed from the inflow path (5a) accumulates in the evaporating chamber (23), causing the liquid level to rise. With this, the float (28) rises and blocks the outflow port to prevent the liquefied gas from flowing out of the outflow path (12). The vaporized gas in the evaporating chamber (23) is thus pressurized, causing the liquid level to be compressed by the pressurizing force and the liquid is in a state to flow back from the inflow port (29) to the inflow path (5a). Here, however, the check valve (25) prevents the liquid from flowing back upstream. At the same time, the pressure in the evaporating chamber (23) increases gradually until it reaches a specified pressure, when the valve (30) operates to feed the gas partially to the bypass (31) to discharge it downstream. Thus, the gas pressure drops and the liquid level lowers to restore the original steady state. Accordingly, the liquefied gas is prevented from directly flowing downstream.

Figure 3:
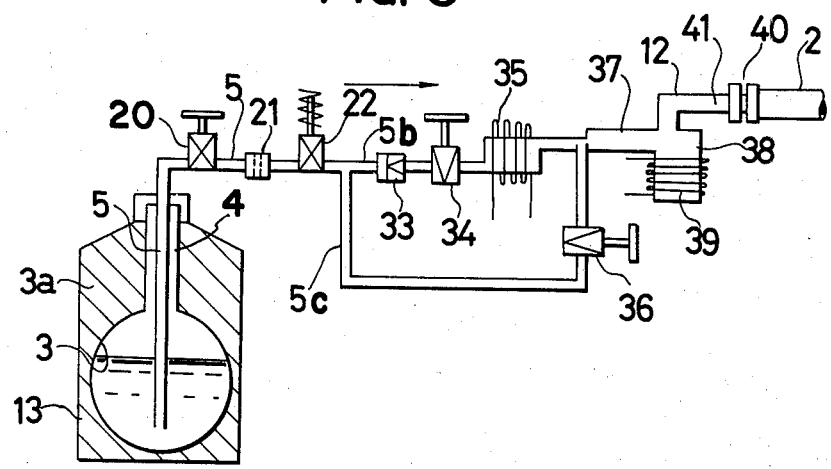
FIG. 3 is a schematic diagram of still another evaporating mechanism according to the present invention.

The evaporating apparatus described in reference to FIG. 1 is used by further improvement as shown by FIG. 3. The flow path from the liquid gas container (13) to the electromagnetic valve (22) is the same as that of the embodiment in FIG. 1 above, while the conduit (5) downstream of the electromagnetic valve is divided into two branches, (5b) and (5c). The conduit (5b) is provided with check valve (33), liquefied gas flow rate regulator (34) and liquefied gas evaporating apparatus (35) and merges into the branch conduit (5c) downstream of the evaporating apparatus (35). The conduit (5c) is provided with regulator (36) of the liquid gas flowing in the conduit (5c) midway thereof. The conduit (5e) merges into the downstream conduit (5e) in a nozzle shape downstream of the evaporating chamber (35) to form a gas-liquid mixing chamber (37). Downstream of the mixing chamber (37) is gas-liquid separating chamber (38), whose outlet is the discharge port (12) and connects to the conduit (2) for treatment of an affected portion by means of connecting pipe (40). The evaporating chamber (35) and gas-liquid separating chamber (38) are so designed that they are heated externally so as to evaporate the liquefied gas. The separating chamber (38) and discharge port (12) are provided with a liquid detector (39) and thermometer (41); and a heater in the evaporating chamber (35) is operated so as to keep the temperature of vaporized liquefied air flowing from the (5b) side above a certain temperature.

Figure 4:
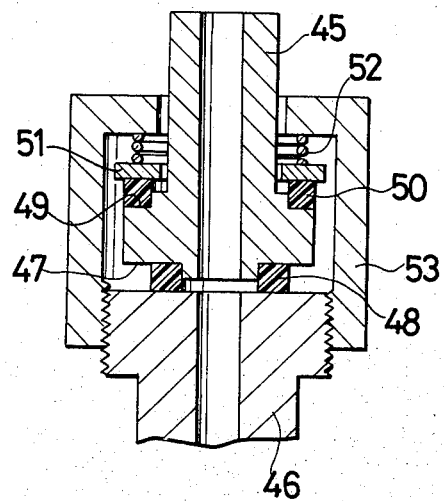
FIG. 4 and FIG. 5 are vertical sections of the joint mechanism.
Figure 5:
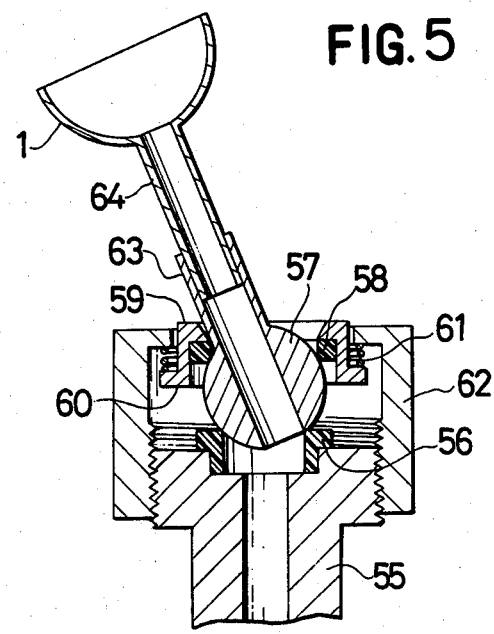
Figure 6:
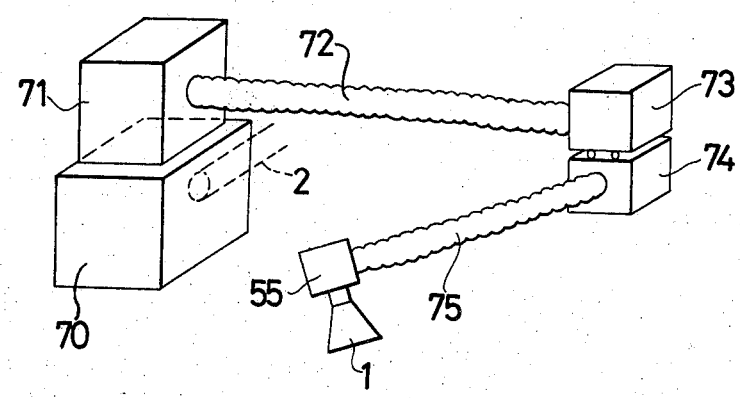
FIG. 6 is a perspective view of the conduit mechanism at the end where gas is required.

The following description is the operation of the evaporating apparatus shown in FIG. 3. As described in reference to the embodiment shown in FIG. 1, the flow of the liquid up to the electromagnetic valve (22) is the same, and part of the liquid that passes through the valve (22) is fed to the evaporating chamber (35) through check valve (33) and flow rate regulator (34). The chamber (35) is heated by a heater and the liquefied gas is vaporized in the chamber (35) and fed to the mixing chamber (37). On the other hand, part of the liquid that passes through the valve (22) is fed to conduit (5c) and to the mixing chamber through flow rate regulator (36). The conduit (5c) is opened in a nozzle shape in the mixing chamber (37) and the velocity of the liquid flowing from the nozzle-shaped discharge port into the mixing chamber is not great. On the other hand, the flow velocity of the liquid vaporized in the evaporating chamber (35) is so great due to volumetric increase during gasification that the liquid flowing in the conduit (5c) is atomized by the liquid flowing in the conduit (5b) and enters the mixing chamber (37), forming a mixture of gas and atomized particles. The mixed fluid is fed to the gas-liquid separating chamber (38) and the gas accumulates in the upper part of the chamber (38) and the fine particles of liquid at the bottom thereof. Here, the gas fed from the evaporating chamber (35) to the mixing chamber (37) in the form of gas is heated considerably, say, −90° C. to 140° C., but is cooled down to a specified cryogenic temperature, say, to −170° C. by being mixed with the liquid in the mixing chamber and is fed to the separating chamber (38). Then the mixture is separated into gas and liquid by specific gravity and viscosity etc. in the separating chamber (38) and the gas is cooled down to a specified temperature to be fed from the discharge port (12) to the conduit (2) through the connecting pipe (40). If the liquid accumulates in the bottom of the separating chamber (38) and is not evaporated completely, the detector (39) detects same and causes the separating chamber (38) to be heated by a heater to evaporate the liquid gas. The discharge port (12) is provided with a temperature sensor (41) to actuate the heater element of the evaporating chamber (35) in accordance with the temperature of the gas passing through the discharge port (12). In this manner, the liquid passing through the conduit (5b) cannot only be vaporized rapidly, but also the liquid passing through the conduit (5c) not heated can be mixed with the vaporized gas in the form of vapor at cryogenic temperature and the temperature of the overheated gas can be lowered rapidly to a specified temperature; thereby gas for medical treatment of an affected portion can be prepared rapidly. As referred to in the preceding paragraph, the vaporized gas is as low as −170° C. in temperature. For the conduit for feeding the gas, a rigid tube is used, as mentioned in the foregoing paragraph. On one end of the rigid tube is provided the cup (1), and mechanisms illustrated in FIGS. 4 to 6 are used to bring the cup (1) close to the affected portion of a patient in a stationary position. In FIG. 4, numerals (45) and (46) are hollow joint tubes to be installed by alignment and a ring-shaped packing (48) of smooth, elastic material such as polytetrafluoroethylene is provided on the shoulder (47) of the joint (45) on the side where both joints face each other and both joints are joined oppositely with packing therebetween. Ring-shaped packing (50), similar to the packing (48) is provided on the shoulder (49) of the joint (45) on the side opposite the packing (48), and washer (51) and coiled spring (52) are placed on the packing (50). Here, both joints are joined by fitting the pot-shaped cylindrical union (53), whose inner wall is partially threaded, to the threaded portion of the outer wall of the joint (46), with the inner bottom of the pot (53) urged toward the spring (52). This makes the joint (45) coaxial with the joint (46) and allows it to rotate with respect to the joint (46). To describe another joint further, referring to FIG. 5, ring-shaped packing (56) similar to the above is provided on the shoulder in the upper part of the hollow joint (55), and hollow spherical body (57) which can be made coaxial with the hollow axis of the joint (55) is laid on the joint (55). The joint (55) is joined with the spherical body (57) in such a manner that after arranging the other ring-shaped packing (58) around the spherical body on the opposite side of the packing (56), arranging snap ring (59) having inwardly and outwardly directed flanges on both sides, respectively, around the packing, and arranging coiled spring (61) by placing it on the outwardly directed flange (60) on the outside periphery of the ring (59), the pot-shaped cylindrical union (62) is inserted from the side of the spherical body (57) to fit the thread on the inner wall of the union into the thread of the outer wall of the joint (55). The spherical body has a protrusion of a hollow cylinder (63) in the longitudinal direction of the hollow shaft and the cylinder is fitted with jet pipe (64) which forms an integral part of the cup (1). In this mechanism, the integral part of the spherical body (57) and cylinder (63) along with the joint (55) forms a spherical joint and not only revolves around the joint axis but also can make conical movement with respect to the center of the spherical body so long as the cylinder (63) is in contact with the ring (59). FIG. 6 is a schematic illustration of the joint fitted to the end mechanism, in which stand (70) is provided on the end of the conduit (2) in such a manner that it is air-tight to the conduit (2) and can turn around the conduit axis. If stand (71) is installed, in the same relationship as the joints (45) and (46) in FIG. 4, with respect to the stand (70), the rigid conduit (72) which protrudes from the stand (71) intersecting the conduit (2) at right angles can take a three-dimensional position with respect to the conduit (2). By arranging the stand (73) and stand (74) installed on the end of the conduit (72) in the same relationship as stands (70) and (71), the rigid conduit (75) protruding air-tightly from the stand (74) can be brought close to the affected portion of a patient with respect to the conduit (2). Further provision of the mechanism illustrated in FIG. 5 on the end of the conduit (75) makes it possible to spray cryogenic gas by moving the cup around the leg or knee of a patient in a prone position.

As described above, the art of the present invention vaporizes liquefied gas from a liquefied gas reservoir by an evaporating apparatus in a position near the end where treatment is to be made and supplies the vaporized gas from any three-dimensional direction in the required area on the end by using rigid conduits, thus shortening the gas feeding distance from the evaporating apparatus to the required place. If excessive liquid gas should be fed to the evaporating apparatus, the flow rate of the liquid fed is immediately detected in the evaporating chamber and if the rate reaches a specified rate, the valve mechanism upstream of the evaporating chamber is closed so that the liquefied gas does not flow out to the downstream required place before it is vaporized. Here, the liquid fed from the reservoir to the evaporating chamber by the pressure of further vaporized gas is prevented from being forced to return to the reservoir by compression, thereby the liquid in the reservoir is prevented from gushing out wastefully. Furthermore, the gas to be applied to the affected portion can be prepared in a very short time and the treatment can be performed very efficiently. The above description of the invention is intended to be illustrative and not limiting. Various changes or modifications in the embodiments described may occur to those skilled in the art and these can be made without departing from the spirit or scope of the invention as set forth in the claims.

We claim:

1. An apparatus for refrigeration treatment comprising a liquefied gas source, an evaporator for evaporating the liquefied gas at an optimum temperature, an exhaust tube connected between said gas source and said evaporator to conduct the liquefied gas from said gas source to said evaporator, a conduit for introducing the gas vaporized by said evaporator, and a cup provided with a non-return expansion valve attached at the end of said conduit, said cup adapted to apply said vaporized gas to an affected portion of a patient in order to refrigerate said portion with said vaporized gas, said evaporator being provided with an evaporator chamber for evaporating the liquefied gas to a gaseous state to be blown out from the cup at a specified temperature and said conduit being connected to said evaporator by means of an outflow port, wherein said exhaust tube is provided with an electromagnetic valve for preventing the inflow of liquefied gas into said evaporating chamber and said evaporating chamber is provided with a detector element which actuates said electromagnetic valve by sensing a specified level height of the liquid of the liquefied gas fed to said chamber.

2. An apparatus for refrigeration treatment set forth in claim 1, said conduit being a flexible conduit.

* * * * *